United States Patent
Takiuchi et al.

(10) Patent No.: US 6,307,081 B1
(45) Date of Patent: Oct. 23, 2001

(54) HYPERBRANCHED POLYMERS AND METHODS FOR THE PREPARATION, CURE, AND STABILIZATION THEREOF

(75) Inventors: Kyosuke Takiuchi; Tadashi Okawa, both of Chiba Prefecture (JP); Stephen Edward Cray, Vale of Glamorgan (GB); Aziz Muzafarow, Moscow (RU)

(73) Assignee: Dow Corning Silicone Company, Ltd., Tokyo (JP)

( * ) Notice: Subject to any disclaimer, the term of this patent is extended or adjusted under 35 U.S.C. 154(b) by 0 days.

(21) Appl. No.: 09/437,466

(22) Filed: Nov. 10, 1999

Related U.S. Application Data

(63) Continuation-in-part of application No. 09/218,274, filed on Dec. 12, 1998, now Pat. No. 6,140,525, which is a continuation-in-part of application No. 08/977,291, filed on Nov. 24, 1997, now abandoned.

(51) Int. Cl.$^7$ ............................................ C07F 7/08
(52) U.S. Cl. .................. 556/434; 556/452; 556/451; 528/15; 528/28; 528/31
(58) Field of Search ..................... 556/434, 452, 556/451; 528/15, 28, 31

(56) References Cited

U.S. PATENT DOCUMENTS 6,001,945 * 12/1999 Decker et al. .................... 556/436 X
6,140,525 * 10/2000 Okawa et al. ....................... 556/434

* cited by examiner

*Primary Examiner*—Paul F. Shaver
(74) *Attorney, Agent, or Firm*—Catherine U. Brown; Sharon K. Severance

(57) ABSTRACT

This invention relates to a macromonomer and a method for its preparation. The macromonomer has one or more silicon-bonded hydrogen atoms at one molecular chain terminal, and one or more aliphatically unsaturated silicon-bonded organic groups at the other molecular chain terminal. This invention further relates to a method of forming a hyperbranched polymer by polymerizing the macromonomer with a group VIII metal catalyst. The hyperbranched polymers can be used as surfactants, gelling agents, drug delivery systems, and polymeric absorbents.

49 Claims, No Drawings

HYPERBRANCHED POLYMERS AND METHODS FOR THE PREPARATION, CURE, AND STABILIZATION THEREOF

This application is a continuation-in-part of U.S. patent application Ser. No. 09/218,274, now U.S. Pat. No. 6,140,525, filed Dec. 12, 1998 which is a continuation-in-part of U.S. patent application Ser. No. 08/977,291, abandoned.

FIELD OF THE INVENTION

This invention relates to hyperbranched polymers and methods for their preparation by polymerization of macromonomers. This invention further relates to macromonomers and to methods for their preparation.

BACKGROUND OF THE INVENTION

Diorganopolysiloxanes carrying a single aliphatically unsaturated organic group at one molecular chain terminal and silanol at the other terminal are known in the art. Diorganopolysiloxanes of this type can be synthesized, for example, by the anionic polymerization of cyclic siloxane using a lithium catalyst and methacryloxypropyldimethylsilanol as initiator, as disclosed in Japanese Patent Publication Kokai Number Hei 1-98631. Alternatively, diorganopolysiloxanes of this type can be synthesized by the polymerization of cyclic trisiloxane on the alkali metal salt of methacryloxypropyldimethylsilanol with termination of the polymerization by acetic acid, as disclosed in Japanese Patent Publication Kokai Number Hei 2-92933. However, neither of these methods can synthesize a macromonomer carrying 2 or 3 aliphatically unsaturated organic groups at one molecular chain terminal and silanol or various other functional groups at the other molecular chain terminal.

In addition, macromonomers carrying 2 or 3 aliphatically unsaturated organic groups at the molecular chain terminals and in which siloxane units are bonded across a divalent hydrocarbon group are known as a starting substance for ultraviolet curing as disclosed in Japanese Patent Publication Number Sho 63-183930. The organopolysiloxane-type polymer disclosed is synthesized by the platinum-catalyzed addition reaction of methyldichlorosilane to α,ω-divinyldimethylsiloxane followed by reaction of the product with acryloxymethyldimethylsilanol in the presence of an HCl scavenger. Thus, this synthesis method can provide only organopolysiloxane-type polymers having the same number of aliphatically unsaturated organic groups at both molecular chain terminals, and this method is also incapable of introducing different organic groups in a controllable manner at the two terminals.

Japanese Patent Publication Kokai Number Hei 10-158406 discloses an organopolysiloxane-type polymer that carries 1 aliphatically unsaturated organic group at one molecular chain terminal and 2 or 3 diorganohydrogensiloxy groups at the other chain terminal. Highly branched polysiloxanes (hyperbranched polymers) can be synthesized, for example, by the platinum-catalyzed addition reaction of this organopolysiloxane-type polymer. However, when the highly branched polysiloxane product is held in long-term storage, the silicon-bonded hydrogen atoms in the polymer gradually undergo hydrolysis and condensation due to the platinum catalyst. The result is an increase in the molecular weight, which makes it impossible to produce this polymer in a constant molecular weight form.

Therefore, it is an object of this invention to provide a novel macromonomer that carries 2 or 3 aliphatically unsaturated organic groups at one molecular chain terminal, carries silanol or various other functional groups at the other terminal, and contains siloxane units bonded across a divalent hydrocarbon group. Another object of the present invention is to provide methods for the synthesis of this novel macromonomer.

It is a further object of this invention to provide a hyperbranched polymer made from a macromonomer. Hyperbranched refers to a class of very highly branched polymers which tend to be globular in form. Various types of hyperbranched polymers, which are represented by the Starburst™ dendrimers (treelike polymers), are known. These hyperbranched polymers have higher functional group densities per molecular unit than straight-chain polymers and conventional branched polymers. Another characteristic feature of the hyperbranched polymers is that they possess an internal space once they have been elaborated to several generations. These characteristics point to potential applications as surfactants, gelling agents, drug delivery systems, polymeric absorbents, and the like.

Additionally, introduction of the siloxane bond into the hyperbranched polymer format could provide a hyperbranched polymer that possesses the unique features of polysiloxanes. Various polysiloxane-based hyperbranched polymers have already been proposed. Hyperbranched siloxane polymers can have a SiH surface or an alkenyl or alkynyl surface. However, it is difficult to prepare hyperbranched polymers with a SiH surface because of several factors, including the instability of the SiH precursors, difficulty in controlling the reaction to prevent crosslinking, and difficulty in preventing side reactions during storage. For example, JP-A 03-263,431 teaches a method for synthesizing a SiH-functional polysiloxane dendrimer by repeating a multi-step reaction that includes condensation of the SiCl and SiOH groups and hydrolysis of the SiH group. This method, however, is unsuitable for large-scale industrial production due to its complex synthetic procedure and low overall yield.

In *Organometallic News,* 40–42 (1993), a method is proposed for the synthesis of a SiH-functional polysiloxane dendrimer by reacting polyfunctional chlorosilane with 1,1,3,3-tetramethyldisiloxane in the presence of hydrochloric acid to replace the chlorine atom of SiCl with the dimethylsiloxy group. Since these synthetic methods are each multi-step reactions with isolation and purification at each step, they offer the advantage of producing dendrimers with defined structures and narrow molecular weight distributions. However, they require repetition of the reaction process a number of times in order to obtain dendrimer of the desired generation and they have low overall yields, and these features make them very unsuitable for large-scale industrial production.

Hyperbranched poly(siloxysilanes) are described by Mathias and Carothers in J. Am. Chem. Soc. 1991, 113, 4043–4044. A monomer of the formula $Vi(CH_2)Si(OSiMe_2H)_3$, where Vi is vinyl and Me is methyl, is polymerized using a platinum hydrosilylation catalyst. The resulting hyperbranched polymer with a SiH surface can be stabilized by capping with allylphenylether.

In contrast, in *J. Inorg. Organomet. Polym.* 4(1), 61–77 (1994) a single-step method is proposed for obtaining SiH-functional or Si-vinyl-functional hyperbranched polysiloxane by the intermolecular hydrosilylation reaction of vinyltris(dimethylsiloxy)silane or tris(vinyldimethylsiloxy)silane. While this method cannot provide a narrow molecular weight distribution or defined-structure dendrimer, it nevertheless offers the advantage of providing a Si-functionalized hyperbranched polysiloxane in a single step and has the potential for large-scale industrial production.

Due to the close proximity of the silicon-bonded hydrogen and vinyl in this method, steric hindrance increases in association with the development of the hydrosilylation reaction to such a degree that bringing the reaction to completion becomes quite problematic. In addition, this method has been unable to bring the properties characteristic of polysiloxanes to the hyperbranched polymer format because it gives polymer that has the silethylenesiloxane structure.

As a consequence, a highly reactive, SiH-functional polysiloxane that can provide SiH-functional hyperbranched polysiloxane in a single step is desired. Specifically, a further object of this invention is to provide an organopolysiloxane macromonomer and a method for its preparation. The macromonomer carries an aliphatically unsaturated organic group at one molecular chain terminal and silicon bonded hydrogen atoms at the other terminal. A further object of the invention is to provide a hyperbranched polymer by polymerizing the macromonomer. A further object of this invention is to provide a method for stabilizing the hyperbranched polymer.

SUMMARY OF THE INVENTION

This invention relates to a macromonomer having one or more aliphatically unsaturated organic groups at one molecular chain terminal and having siloxane units bonded across a divalent hydrocarbon group. This invention further relates to methods for synthesizing and polymerizing the macromonomer to form a hyperbranched polymer, and also to a method for stabilizing the hyperbranched polymer.

DETAILED DESCRIPTION OF THE INVENTION

This invention relates to a macromonomer having the general formula:

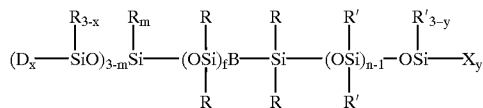

wherein each D is independently an aliphatically unsaturated organic group, each R is independently selected from the group consisting of monovalent hydrocarbon groups free of aliphatic unsaturation and monovalent halogenated hydrocarbon groups free of aliphatic unsaturation; each R' is independently selected from the group consisting of monovalent hydrocarbon groups and monovalent halogenated hydrocarbon groups, B is selected from the group consisting of an oxygen atom and a divalent hydrocarbon group having at least two carbon atoms and free of aliphatic unsaturation; each X is independently selected from the group consisting of hydroxyl groups and monovalent organosiloxy- groups containing a silicon-bonded functionality. The silicon-bonded functionality is selected from the group consisting of a hydrogen atom, alkenyl groups, acryloxy groups, methacryloxy groups, vinylphenyl groups, primary amino groups, and secondary amino groups; n is an integer with a value of 1 to 1,001; x is 1, 2, or 3; m is 0, 1, or 2;f is an integer with a value greater than or equal to 0; and y is 1, 2, or 3.

D is an aliphatically unsaturated organic group. D is exemplified by alkenyl groups such as vinyl, butenyl, and hexenyl; alkenyloxyalkyl groups such as allyloxyethyl and methacryloxypropyl; alkynyl groups; and 4-vinylphenyl. D is preferably an alkenyl group or an alkynyl group containing 2 to 6 carbon atoms. D is more preferably vinyl or allyl, with the proviso that the unsaturation of the allyl group is terminal. Vinyl is particularly preferred due to ease of synthesis and economics.

Each R is independently selected from the group consisting of monovalent hydrocarbon groups free of aliphatic unsaturation and monovalent halogenated hydrocarbon groups free of aliphatic unsaturation. Examples of monovalent hydrocarbon groups for R include alkyl such as methyl, ethyl, propyl, butyl, pentyl, and hexyl; aryl such as phenyl, tolyl, and xylyl; and aralkyl groups such as benzyl and phenethyl. Monovalent halogenated hydrocarbon groups are exemplified by trifluoropropyl. Preferably, each R is independently selected from the group consisting of alkyl groups of i1 to 6 carbon atoms, halogenated alkyl groups of 1 to 6 carbon atoms, and phenyl groups. Methyl is particularly preferred for R.

Each R' is independently selected from monovalent hydrocarbon groups. R' is exemplified by the same groups provided as examples of R, but R' can also be an alkenyl group such as vinyl, allyl, or hexenyl.

B is selected from the group consisting of oxygen and divalent hydrocarbon groups having at least 2 carbon atoms and free of aliphatic unsaturation. Examples of divalent hydrocarbon groups for B include ethylene, methylethylene, butylene, and hexylene. B is preferably ethylene.

X is selected from the group consisting of a hydroxyl group, a monovalent siloxy group of the formula —OSi(R$_2$)Z, and a monovalent siloxy group of the formula

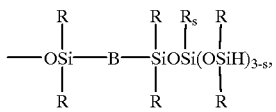

wherein s is 0 or 1.

In the monovalent siloxy group having the formula —OSi(R$_2$)Z, Z is selected from the group consisting of a hydrogen atom, alkenyl groups, acryloxy groups, methacryloxy groups, vinylphenyl groups, primary amino groups, and secondary amino groups. The alkenyl group for Z is exemplified by vinyl, allyl, and hexenyl; the primary amino is exemplified by 3-aminopropyl; and the secondary amino is exemplified by 3-N-methylamino-2-methylpropyl and N-tert-butylaminopropyl. R and B are as defined above. Different types of functional groups preferably reside at the two terminals of the macromonomer of this invention.

In the formula for the macromonomer,f is an integer with a value greater than or equal to 0. Preferably,f is 0 to 1,000, more preferably 0 to 200, more preferably 1 to 100, and particularly preferably 10 to 100.

In the formula for the macromonomer, the subscript m is 0, 1, or 2 and n is an integer with a value greater than or equal to 1. Preferably n is 1 to 1,001; more preferably, n is 1 to 501 ; and more preferably, n is 1 to 201.

In the formula for the macromonomer, the subscript x is 1, 2, or 3, and y is 1, 2, or 3. When the subscript m is 2, n must be 1, X must be —OSiR$_2$Z, and Z must be hydrogen; with the provisos that when m is 2, if x is 1, y is 2 or 3 and if y is 1, x is 2 or 3.

In one embodiment of this invention, the macromonomer contains 2 or 3 silicon-bonded aliphatically unsaturated organic groups (i.e., when m is 0 or 1) at one molecular chain terminal and silanol or other functional groups at the other terminal. This macromonomer preferably has the formula:

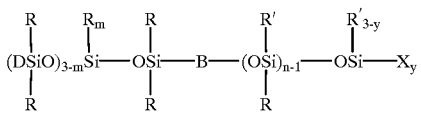

wherein D is an aliphatically unsaturated organic group, each R is independently a monovalent hydrocarbon group free of aliphatic unsaturation, each R' is independently a monovalent hydrocarbon group, B is a divalent hydrocarbon group with at least two carbon atoms and free of aliphatic unsaturation, n is 1 to 1,001, and y is 1, 2, or 3.

In this embodiment of the invention, D is exemplified by alkenyl groups such as vinyl, butenyl, and hexenyl; alkenyloxyalkyl groups such as allyloxyethyl; the methacryloxypropyl group; and the 4-vinylphenyl group, among which alkenyl is preferred from the standpoints of economics and ease of synthesis. Vinyl is particularly preferred for D. R is exemplified by alkyl groups such as methyl, ethyl, propyl, butyl, pentyl, and hexyl; aryl groups such as phenyl, tolyl, and xylyl; and aralkyl groups such as benzyl and phenethyl. Methyl is particularly preferred for R based on ease of acquisition and economics. R' is exemplified by the same groups provided as examples of R, but R' can also be an alkenyl group such as vinyl, allyl, or hexenyl. B is exemplified by ethylene, methylethylene, butylene, and hexylene. The subscript n is preferably 1 to 501 and more preferably 1 to 201.

In this embodiment of the invention, X can be a hydroxyl group or a monovalent organosiloxy group of the formula —OSi(R$_2$)Z, wherein Z is a functional group selected from the group consisting of alkenyl, acryloxy, methacryloxy, vinylphenyl, silicon-bonded hydrogen, primary amino, and secondary amino. This alkenyl can be exemplified by vinyl, allyl, and hexenyl; the primary amino can be exemplified by 3-aminopropyl; and the secondary amino can be exemplified by 3-N-methylamino-2-methylpropyl and N-tert-butylaminopropyl. X can also be a monovalent organosiloxy group of the formula

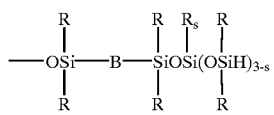

wherein R and B are as defined above and s is 0 or 1. Different types of functional groups preferably reside at the two terminals of the macromonomer in this embodiment of the invention.

The macromonomer in this embodiment of the invention is exemplified by macromonomers with the following structural formulas:

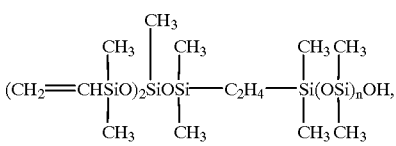

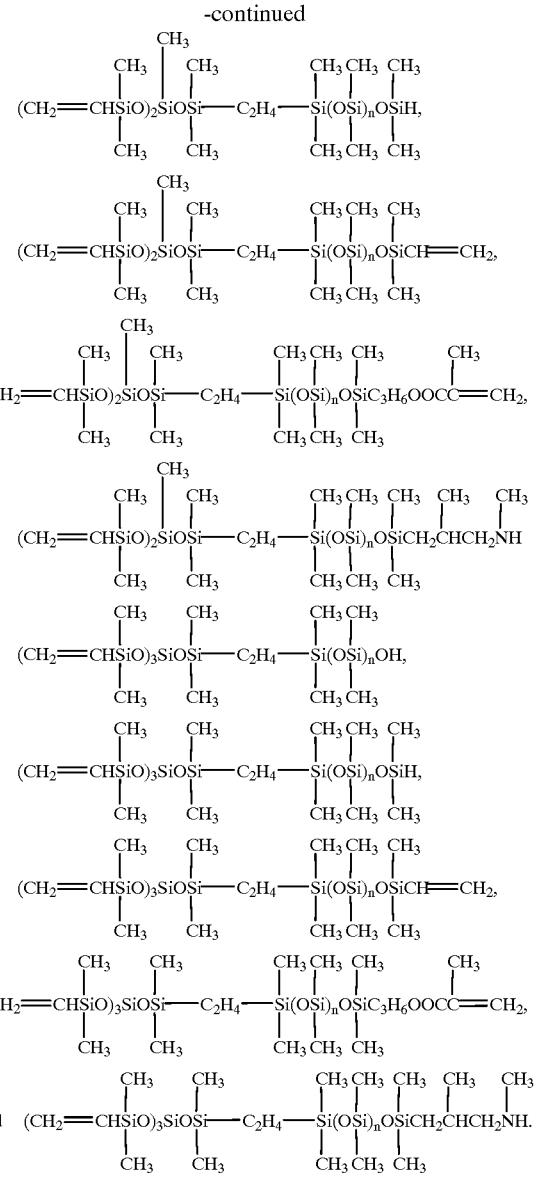

In this embodiment of the invention, the macromonomer is useful as a reactive diluent, as a reaction accelerator, as a modulus-control agent, and as an intermediate for the modification of organic resins because it contains 2 or 3 silicon-bonded aliphatically unsaturated organic groups at one molecular chain terminal and silanol or the various other functional groups at the other terminal. When the macromonomer contains 2 or 3 silicon-bonded aliphatically unsaturated organic groups at one molecular chain terminal and contains silicon-bonded hydrogen at the other molecular chain terminal, the macromonomer is very well-suited for use as a starting reagent for highly branched polysiloxanes (hyperbranched polymers), and the hyperbranched polymer afforded by the platinum-catalyzed addition reaction of this organopolysiloxane-type polymer has an excellent storage stability.

In an alternative embodiment of the invention, the macromonomer can have only one aliphatically unsaturated group (e.g., when m is 2 and x is 1) at one molecular chain terminal and more than one silicon-bonded hydrogen atom containing group at the other chain terminal. In this embodiment, the macromonomer preferably has the formula:

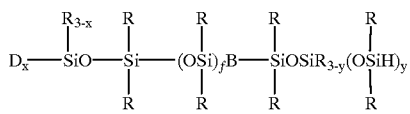

wherein D is an aliphatically unsaturated organic group, each R is independently selected from the group consisting of monovalent hydrocarbon groups free of aliphatic unsaturation and monovalent halogenated hydrocarbon groups free of aliphatic unsaturation; B is selected from the group consisting of an oxygen atom and a divalent hydrocarbon group of at least two carbon atoms and free of aliphatic unsaturation; f is an integer with a value greater than or equal to 0; x is 1, 2, or 3; and y is 1, 2, or 3.

In this embodiment of the invention D represents an aliphatically unsaturated organic group, for example, alkenyl such as vinyl, butenyl, and hexenyl; alkenyloxyalkyl such as allyloxyethyl, methacryloxypropyl, and 4-vinylphenyl. D is preferably a lower alkenyl or alkynyl group containing 2 to 6 carbon atoms. D is more preferably vinyl or allyl, with the proviso that the unsaturation of the allyl group is terminal. Vinyl is particularly preferred due to ease of synthesis and economics.

Each R is independently selected from the group consisting of monovalent hydrocarbon groups free of aliphatic unsaturation and monovalent halogenated hydrocarbon groups free of aliphatic unsaturation. Examples of monovalent hydrocarbon groups for R include alkyl such as methyl, ethyl, propyl, butyl, pentyl, and hexyl; aryl such as phenyl, tolyl, and xylyl; and aralkyl such as benzyl and phenethyl. Monovalent halogenated hydrocarbon groups are exemplified by trifluoropropyl. R is preferably independently selected from the group consisting of alkyl groups of 1 to 6 carbon atoms, haloalkyl groups of 1 to 6 carbon atoms, and phenyl. Methyl is particularly preferred for R.

B is selected from the group consisting of oxygen and divalent hydrocarbon groups with at least 2 carbon atoms and free of aliphatic unsaturation. The divalent hydrocarbon groups for B are exemplified by ethylene, methylmethylene, propylene, butylene, and hexylene. B is preferably ethylene.

In this embodiment of the invention, x has a value of 1, 2, or 3, y has a value of 1, 2, or 3; with the provisos that when x is 1, y is 2 or 3, and when y is 1, x is 2 or 3. When x is 1, y is 2 or 3, and the macromonomer will have one aliphatically unsaturated organic group at one molecular chain terminal and 2 or 3, respectively, diorganohydrogensiloxy groups at the other molecular chain terminal. When y is 1, x is 2 or 3, and the macromonomer will have one diorganohydrogensiloxy group at one molecular chain terminal and 2 or 3, respectively, aliphatically unsaturated organic groups at the other molecular chain terminal.

Preferably, f ranges from 0 to 1,000, more preferably from 0 to 200, more preferably 1 to 100, and particularly preferably from 10 to 100.

A preferred macromonomer of this embodiment of this invention has the formula

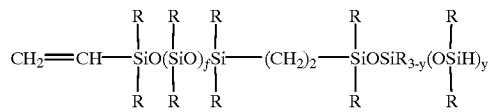

where R, f, and y are as described above.

A particularly preferred macromonomer of this invention has the formula

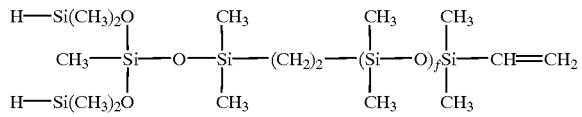

where f is preferably 10 to 100.

This invention further relates to methods for making the macromonomers described above. The methods are exemplified as follows.

One embodiment of this invention relates to a method for synthesizing a macromonomer having 2 or 3 silicon-bonded aliphatically unsaturated organic groups (i.e., when m is 0 or 1) at one molecular chain terminal and silanol or other functional groups at the other terminal. For example, the method for the synthesis of a macromonomer with the formula:

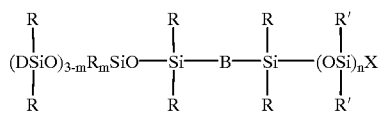

wherein D, R, R', and n are as described for the general formula above, m is 0 or 1, B is a divalent hydrocarbon group and X is selected from the group consisting of a hydroxyl group and a monovalent organosiloxy group having the general formula —(OSiR$_2$Z), wherein Z is selected from the group consisting of a hydrogen atom and a functional group selected from the group consisting of alkenyl, acryloxy, methacryloxy, and vinylphenyl is described below.

This method is characterized by (1) effecting the ring-opening polymerization of (C) a cyclic trisiloxane, using (A) a lithium siloxanolate as a polymerization initiator, and optionally using (B) an organosiloxanol as a molecular weight regulator, and (2) terminating the ring-opening polymerization with (D) a terminating agent. Component (A) is a lithium siloxanolate with the general formula

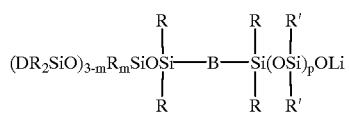

wherein D, m, R, B, and R' are as described above and p is an integer with a value no greater than 10.

Component (B) is an organosiloxanol with the general formula

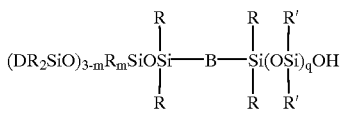

wherein D, m, R, B, and R' are as described above and q is an integer with a value no greater than 10.

Component (C) is a cyclic trisiloxane with the general formula

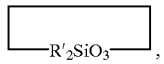

wherein R' is as described above.

Component (D) is a terminating agent selected from the group consisting of acids, SiH-functional compounds that contain the halosilyl group, alkenyl-functional compounds that contain the halosilyl group, acryloxy-functional compounds that contain the halosilyl group, methacryloxy-functional compounds that contain the halosilyl group, and compounds that contain both the vinylphenyl group and a halosilyl group. Using component (D), this method carries out the introduction of a functional group at the same time as the reaction that terminates the ring-opening polymerization.

Another method for the synthesis of macromonomers having 2 or 3 silicon-bonded aliphatically unsaturated organic groups (i.e., when m is 0 or 1) at one molecular chain terminal and silanol or other functional groups at the other terminal is as follows. This method is for the synthesis of a macromonomer with the general formula

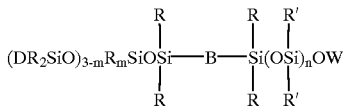

wherein D, R, R', and n are as described above, B is a divalent hydrocarbon group, m is 0 or 1, and W is a monovalent organosilyl group containing a functional group selected from the group consisting of alkenyl, acryloxy, methacryloxy, vinylphenyl, silicon-bonded hydrogen, primary amino, and secondary amino. This method is characterized by (I) effecting the ring-opening polymerization of the cyclic trisiloxane (C) using the lithium siloxanolate (A) as the polymerization initiator and optionally using the organosiloxanol (B) as the molecular weight regulator;

(II) terminating this ring-opening polymerization with (D) a terminating agent that is an acid to synthesize the organopolysiloxane-type polymer with the following formula in which one molecular chain terminal is blocked by aliphatically unsaturated bond-containing organic groups and the other terminal is blocked by silanol

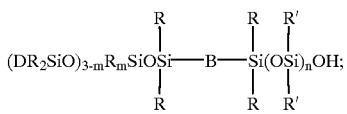

and then (III) reacting this organopolysiloxane-type polymer with (E) an SiH-functional compound that contains a hydrolyzable silyl group, an alkenyl-functional compound that contains a hydrolyzable silyl group, an acryloxy-functional compound that contains a hydrolyzable silyl group, a methacryloxy-functional compound that contains a hydrolyzable silyl group, a compound that contains both the vinylphenyl group and a hydrolyzable silyl group, a cyclic silylamine, or an N-substituted cyclic silylamine.

In step (III) when component (E) is added to the intermediate, a condensation reaction or ring-opening reaction is carried out to give the macromonomer with the formula

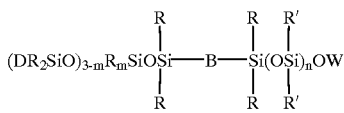

in which D, R, R', B, m, n, and W are defined as above. A ring-opening reaction is run on the intermediate when component (E) is cyclic silylamine or N-substituted cyclic silylamine, and a condensation reaction is run on the intermediate when component (E) is an SiH-functional compound that contains a hydrolyzable silyl group, an alkenyl-functional compound that contains a hydrolyzable silyl group, an acryloxy-functional compound that contains a hydrolyzable silyl group, a methacryloxy-functional compound that contains a hydrolyzable silyl group, or a compound that contains both the vinylphenyl group and a hydrolyzable silyl group.

Examples of component (E) used in this synthesis include the following. SiH-functional compounds that contain a hydrolyzable silyl group are exemplified by dimethylchlorosilane, dimethylacetoxysilane, 1,1,3,3-tetramethyldisilazane, and (diethylamino)dimethylsilane; alkenyl-functional compounds that contain a hydrolyzable silyl group are exemplified by dimethylvinylchlorosilane, dimethylvinylacetoxysilane, 1,1,3,3-tetramethyl-1,3-divinyldisilazane, and (diethylamino)dimethylvinylsilane; acryloxy-functional compounds that contain a hydrolyzable silyl group are exemplified by 3-acryloxypropyldimethylchlorosilane, 3-acryloxypropyldimethylacetoxysilane, 1,1,3,3-tetramethyl-1,3-di(3-acryloxypropyl)disilazane, and 3-acryloxypropyl(diethylamino)dimethylsilane; methacryloxy-functional compounds that contain a hydrolyzable silyl group are exemplified by 3-methacryloxypropyldimethylchlorosilane, 3-methacryloxypropyldimethylacetoxysilane, 1,1,3,3-tetramethyl-1,3-di(3-methacryloxypropyl)disilazane, and 3methacryloxypropyl(diethylamino)dimethylsilane; the vinylphenyl-functional compounds that contain a hydrolyzable silyl group are exemplified by o-vinylphenyldimethylchlorosilane, o-vinylphenyldimethylacetoxysilane, 1,1,3,3-tetramethyl-1,3-di(o-vinylphenyl)disilazane, o-vinylphenyl(diethylamino)dimethylsilane, m-vinylphenyldimethylchlorosilane, m-vinylphenyldimethylacetoxysilane, 1,1,3,3tetramethyl-1,3-di(m-vinylphenyl)disilazane, m-vinylphenyl(diethylamino)dimethylsilane, p-vinylphenyldimethylchlorosilane, p-vinylphenyldimethylacetoxysilane, 1,1,3,3-tetramethyl-1,3-di(p-vinylphenyl)disilazane, and p-vinylphenyl(diethylamino)dimethylsilane; and the cyclic silylamines are exemplified by compounds with the formula

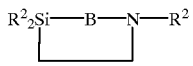

wherein $R^2$ is a hydrogen atom or a monovalent hydrocarbon group and B is defined as above. The N-substituted cyclic silylamines are exemplified by 1,2,2,4-tetramethyl-1-aza2-silacyclopentane. Methods for the synthesis of these cyclic silylamines and N-substituted cyclic silylamines are known. For example, synthesis can be carried out according to the method of U.S. Pat. No. 3,146,250, hereby incorporated by reference by reacting 3-chloro-2-methylpropyldimethylchlorosilane and methylamine.

The lithium siloxanolate (A), described above, can be synthesized by reacting an organosiloxanol with the formula

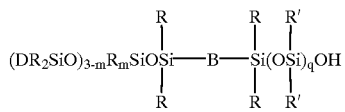

wherein D, R, R', and m are defined as above, B is a divalent hydrocarbon group, and q is integer with a value no greater than 10; with a lithium compound such as an alkyllithium, exemplified by n-butyllithium, methyllithium, sec-butyllithium, and tert-butyllithium, or an aryllithium, exemplified by phenyllithium.

The organosiloxanol (B) can be synthesized, for example, by the route given below. A hydrosilylation reaction is run between an oligosiloxane having at least 3 aliphatically unsaturated bonds and a hydridosilane bearing a silicon-bonded hydrolyzable group. Only the 1:1 addition product is isolated and purified, for example, by distillation, from the reaction product and then hydrolyzed by a known method.

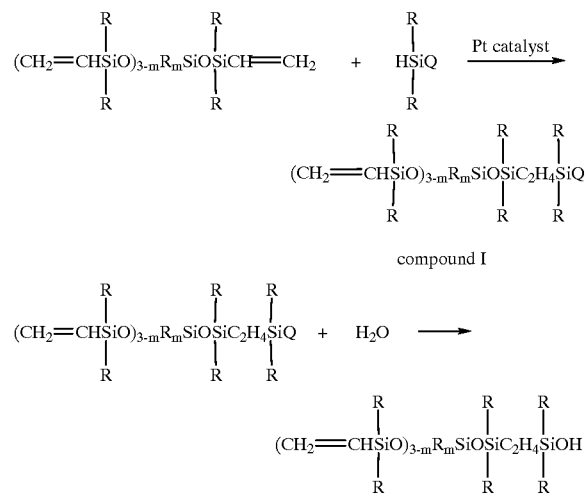

The organosiloxanol (B) can also be synthesized, as shown below, by first running a reaction between compound I (see above) and cyclic trisiloxane and then hydrolyzing the reaction product.

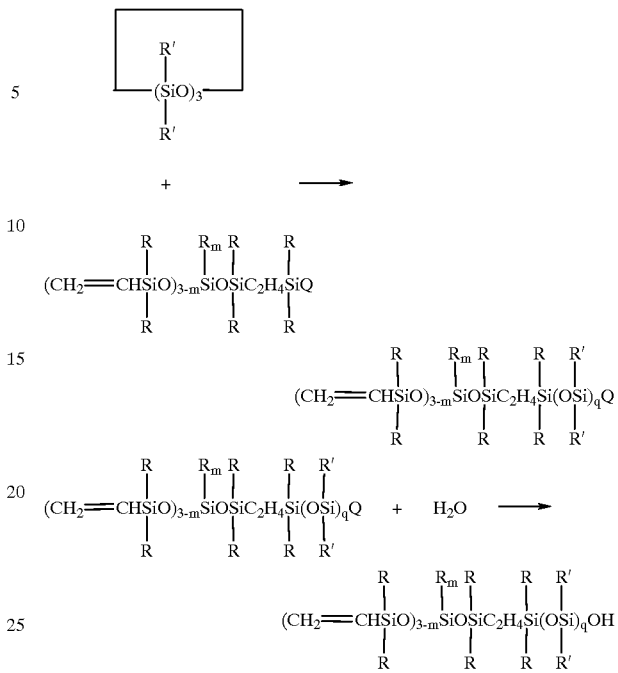

R, R', m, and q in the preceding formulas are the same as defined above, while Q is a hydrolyzable group selected from halogen atoms, amino, substituted amino, and acyloxy.

The cyclic trisiloxane (C) has the general formula given above. While R' in this general formula is defined as above, methyl and phenyl are preferred for R' due to ease of acquisition, with methyl being particularly preferred. The cyclic trisiloxane (C) can be exemplified by compounds with the following formulas:

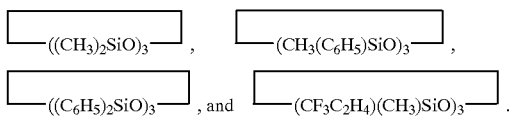

When the particular cyclic trisiloxane (C) used takes the form of a solid, an organic solvent is preferably used to be able to run the intended polymerization reaction in a homogeneous system. This organic solvent should be an aprotic solvent. Highly suitable examples are aromatic hydrocarbons such as benzene, toluene, and xylene; aliphatic hydrocarbons such as hexane and pentane; ethers such as tetrahydrofuran and diethyl ether; ketones such as acetone and methyl ethyl ketone; esters such as ethyl acetate and butyl acetate; and also dimethylformamide, dimethyl sulfoxide, and hexamethylphosphoric acid triamide. Particularly good results will frequently be obtained by the use of combinations of two or more solvents. For example, when a weakly polar solvent such as toluene is employed, a highly polar solvent (e.g., dimethylformamide, dimethyl sulfoxide, or hexamethylphosphoric acid triamide) is preferably used to accelerate the reaction.

The temperature of the polymerization reaction in the methods for preparing the macromonomers, discussed above, of this invention must be controlled with careful consideration given to minimizing the occurrence of siloxane bond rearrangement reactions. The occurrence of rearrangement reactions results in the secondary production of organopolysiloxane-type polymers other than the desired macromonomer having 2 or 3 aliphatically unsaturated organic groups at one molecular chain terminal and silanol or the lithium siloxanolate group at the other terminal. These by-products include organopolysiloxane-type polymers having 2 or 3 aliphatically unsaturated organic groups at both terminals and organopolysiloxane-type polymer having silanol or the lithium siloxanolate group at both terminals. Relatively low temperatures are recommended to restrain siloxane bond rearrangement reactions. Specifically, the range of 0 to 100° C. is preferred, while the range of 0 to 70° C. is even more preferred. Preferably, the moisture in the solvent and starting reagents is removed to the greatest extent possible prior to polymerization. The presence of moisture results in a reduction in the molecular weight of the macromonomer product and in the secondary production of organopolysiloxane-type polymer bearing silanol at both terminals. The lithium siloxanolate (A) polymerization initiator need only be added to the polymerization reaction in sufficient quantity to induce the ring-opening polymerization of the cyclic trisiloxane (C). The lithium siloxanolate (A): organosiloxanol (B) molar ratio should be from 100:0 to 0.01:99.99. This molar ratio is preferably from 0.5:99.5 to 50:50 based on considerations of economizing on the high-value catalyst while obtaining a good polymerization rate.

Component (D) the terminating agent for the polymerization reaction functions to terminate the ring-opening polymerization of component (C). Component (D) is selected from acids, SiH-+halosilyl-functional compounds, alkenyl-+halosilyl-functional compounds, acryloxy-+halosilyl-functional compounds, methacryloxy-+halosilyl-functional compounds, and vinylphenyl-+halosilyl-functional compounds.

The acids are exemplified by wet carbon dioxide, mineral acids such as hydrochloric acid and sulfuric acid, and organic acids such as acetic acid, propionic acid, and other carboxylic acids. When the acid is used in excess relative to the lithium siloxanolate (A), a weak acid is preferably employed to inhibit siloxane rearrangement reactions in the macromonomer product that could be induced by the excess acid. The use of wet carbon dioxide or acetic acid is most preferred in these circumstances.

The SiH- and halosilyl-functional compounds are exemplified by hydridohalosilanes such as dimethylchlorosilane, diethylchlorosilane, diphenylchlorosilane, dimethylbromosilane, and others, and by the bis(dimethylsiloxy)halosilethylenesiloxane and tris(dimethylsiloxy)halosilethylenesiloxane. The structural formulas are given below and are disclosed in U.S. Pat. No. 5,175,328, hereby incorporated by reference:

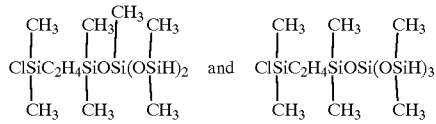

The alkenyl-+halosilyl-functional compounds are exemplified by vinyldimethylchlorosilane, hexenyldimethylchlorosilane, and divinylmethylchlorosilane.

The acryloxy-+halosilyl-functional compounds are exemplified by acryloxypropyldimethylchlorosilane, acryloxyhexyldimethylchlorosilane, acryloxyethoxypropyldimethylchlorosilane, and acryloxypropyldimethylbromosilane.

The methacryloxy-+halosilyl-functional compounds are exemplified by methacryloxypropyldimethylchlorosilane, methacryloxyhexyldimethylchlorosilane, methacryloxyethoxypropyldimethylchlorosilane, and methacryloxypropyldimethylbromosilane.

The vinylphenyl-+halosilyl-functional compounds are exemplified by 4-vinylphenyldimethylchlorosilane, 4-vinylphenyldimethylbromosilane, and 2-vinylphenyldimethylchlorosilane.

The use of an acid such as wet carbon dioxide, mineral acid, or carboxylic acid as component (D) to stop the ring-opening polymerization will give an organopolysiloxane-type polymer that carries 2 or 3 silicon-bonded aliphatically unsaturated organic groups at one molecular chain terminal and silanol at the other terminal. When the ring-opening polymerization is stopped using the various halosilyl-functional compounds as component (D), the product will be a macromonomer that carries 2 or 3 silicon-bonded aliphatically unsaturated organic groups at one molecular chain terminal and that carries the dehalogenated silyl residue from the particular terminating agent used at the other terminal. A hydrogen halide scavenger, such as an organic amine compound or ammonia, is preferably added in this latter case (use of a halosilyl-functional compound as the terminating agent).

Termination of the polymerization reaction by component (D) is preferably carried out by monitoring the disappearance of the cyclic trisiloxane (C) by, for example, gas chromatography, and conducting the neutralization reaction when the conversion has reached a constant or specified value. In general, lower conversions are associated with a lower occurrence of siloxane bond rearrangement reactions and hence with a better polymer product purity, but also result in lower yields. Higher conversions are accompanied by better yields of the polysiloxane target, but are also accompanied by a greater occurrence of the aforementioned side reactions and hence result in a lower purity for the polysiloxane target. Thus, the conversion at which the polymerization reaction should be terminated must be determined considering both the purity and yield of the desired macromonomer. The optimal conversion cannot be stringently specified because it will vary as a function of the type of cyclic trisiloxane and molecular weight of the polymer product, although generally the conversion will be from 60 to 100% and preferably from 70 to 95%. The cyclic trisiloxane must be polymerized until this conversion is achieved, and the polymerization time will be determined by the reaction temperature and the reactivity of the cyclic trisiloxane. For example, the use of a highly reactive cyclic trisiloxane will make it possible for the desired polymerization to be finished in relatively shorter times at lower temperatures.

The molecular weights of the macromonomers afforded by the methods described above are determined by the ratio between the number of moles of cyclic trisiloxane that have participated in the polymerization reaction and the total number of moles of component (A) (initiator) plus component (B). The molecular weight of the macromonomers after polymerization can be obtained from the following formula.

$$\frac{\begin{array}{c}\text{moles of component } (C) \text{ that have participated} \\ \text{in the polymerization reaction} \\ \left(= \text{moles of component } (C) \times \text{conversion}/100\right)\end{array}}{\text{moles}(A) + \text{moles}(B)}$$

This invention further relates to methods for making a macromonomer where, in he general formula for the macromonomer described above, m is 2, n is 1, R' is R, X is —OSi(R$_2$)Z, and Z is hydrogen, whereby the macromonomer has the general formula:

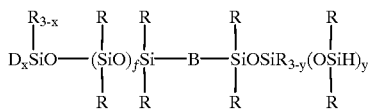

wherein D, R, and f are as described above. B is selected from the group consisting of oxygen and divalent hydrocarbon groups with at least 2 carbon atoms and free of aliphatic unsaturation. B is exemplified by ethylene, methylmethylene, propylene, butylene, and hexylene. B is preferably ethylene. The subscript x has a value of 1, 2, or 3, the subscript y has a value of 1, 2, or 3; with the provisos that when x is 1, y is 2 or 3, and when y is 1, x is 2 or 3. When x is 1, y is 2 or 3, and this macromonomer will have one aliphatically unsaturated organic group at one molecular chain terminal and 2 or 3, respectively, diorganohydrogensiloxy groups at the other molecular chain terminal. When y is 1, x is 2 or 3, and the macromonomer will have one diorganohydrogensiloxy group at one molecular chain terminal and 2 or 3, respectively, aliphatically unsaturated organic groups at the other molecular chain terminal.

The method comprises (i) reacting component (a), which has general formula

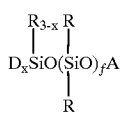

where D, R, x, and f are as defined above, and A is selected from the group consisting of a hydrogen atom, an alkali metal atom, and combinations thereof; and component (b), which has general formula

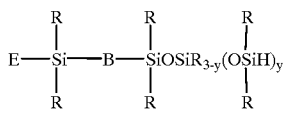

where R, B, and y are as defined above and E is selected from the group consisting of halogen atoms, amino groups, substituted amino groups, and acyloxy groups. Preferably, the halogen atom is chlorine and the alkali metal atom is lithium.

Component (a) may be an organosilane or an organosiloxane or a mixture thereof. Component (a) can be synthesized by the living polymerization of cyclic hexaorganotrisiloxane using a lithium metal salt of an aliphatically unsaturated silanol or siloxanol or a partially lithiated aliphatically unsaturated silanol or siloxanol. Synthesis of component (a) by this method is described in U.S. Pat. No. 4,976,373, hereby incorporated by reference. When A is a hydrogen atom, component (a) is an organopolysiloxane bearing silanol at one molecular chain terminal. This type of component (a) can be synthesized by treating the α-lithiooxyorganopolysiloxane or partially lithiated α-hydroxyorganopolysiloxane synthesized as described above with, for example, acetic acid or carbonic acid.

Component (b) is an organosilicon compound. The hydrolyzable group, E, on component (b) is selected from the group consisting of halogen atoms, amino groups, substituted amino groups, and acyloxy groups. The hydrolyzable group is specifically exemplified by halogen atoms such as fluorine, chlorine, bromine, and iodine; the amino group; substituted amino groups such as ethylamino, diethylamino, substituted silylamino, and substituted siloxanylamino; and acyloxy groups such as acetoxy and propionyloxy.

Silazane derivatives with the structures given below can be used as component (b) in this invention. The silazanes can be synthesized by reacting ammonia and the corresponding chlorosiloxane compound, as shown in the following equation:

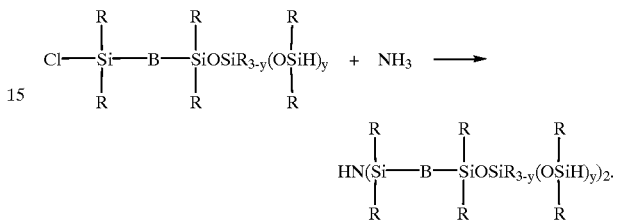

Alternatively, the silazanes can be synthesized by a hydrosilylation reaction between silazane containing aliphatically unsaturated bonding and oligosiloxane bearing multiple SiH functionalities, as shown in the following equation:

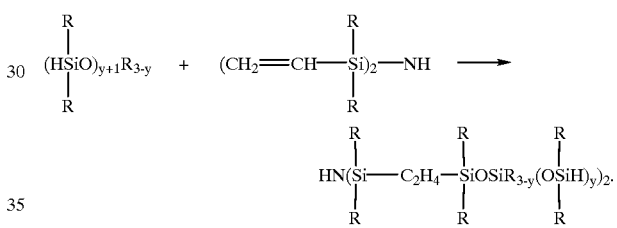

Among the examples of E, the chlorine atom and diethylamino group are preferred due to ease of synthesis, reactivity, and economics. The chlorine atom is particularly preferred.

Alternatively, component (b) can be synthesized by addition reaction of a silicon compound that contains 3 or 4 diorganohydrogensiloxy groups in each molecule with a silane that contains an Si-bonded hydrolyzable group and aliphatically unsaturated bonding in the same molecule and by subsequent purification by distillation to isolate the 1:1 adduct. The 1:1 adduct can be obtained in good yields from this reaction by improving the reaction selectivity with at least the stoichiometric amount of the former reagent relative to the latter reagent. A stoichiometric ratio in the range of equivalency to 3-times equivalency is preferred.

This addition reaction is catalyzed by a catalyst comprising a Group VIII metal that is suitable for use in hydrosilylationreactions. Examples of suitable catalysts are ruthenium, rhodium, palladium, osmium, iridium and platinum. Preferably the catalyst is a platinum compound or complex. Suitable platinum compounds and complexes include chloroplatinic acid and its alcohol solutions, platinum acetylacetonate, complexes of platinous halides with unsaturated compounds such as ethylene, propylene, organovinylsiloxanes, and styrene, hexamethyldiplatinum, PtCl$_2$, PtCl$_3$, PtCl$_4$, and Pt(CN)$_3$.

The addition reaction can be run in the absence of solvent or in a suitable organic solvent. Specific examples of organic solvents include aromatic hydrocarbons such as benzene, toluene, and xylene; aliphatic hydrocarbons such as hexane and heptane; ethers such as tetrahydrofuran and diethyl ether; ketones such as acetone and methyl ethyl ketone; esters such as ethyl acetate and butyl acetate; chlorinated hydrocarbons such as carbon tetrachloride, trichloroethane, and chloroform; as well as dimethylformamide and dimethyl sulfoxide. This addition reaction can be run at room temperature, but it is preferably run at 50° C. to 200° C.

The method of forming the macromonomer can be carried out by reacting a composition comprising components (a) and (b) by condensation reaction. The condensation reaction between components (a) and (b) should be run using at least one equivalent of component (b) relative to component (a) and preferably at least 1.05 equivalents of component (b) relative to component (a). The condensation reaction is preferably run at 0° C. to 200° C. and more preferably at 20° C. to 100° C. The condensation reaction can be run without solvent, but it is preferably run in the presence of a suitable organic solvent. Suitable organic solvents are specifically exemplified by aromatic hydrocarbons such as benzene, toluene, and xylene; aliphatic hydrocarbons such as hexane and heptane; ethers such as tetrahydrofuran and diethyl ether; ketones such as acetone and methyl ethyl ketone; esters such as ethyl acetate and butyl acetate; chlorinated hydrocarbons such as carbon tetrachloride, trichloroethane, and chloroform; as well as dimethylformamide and dimethyl sulfoxide.

When component (a) is a mixture that contains both hydrogen and alkali metal atoms for different instances of A, and component (b) is an organosilicon compound in which E is a halogen atom, an amine compound is preferably added as a hydrogen halide scavenger to inhibit equilibration reactions by the organopolysiloxane chain under the influence of the hydrogen halide by-product generated by this reagent combination. These amine compounds are exemplified by triethylamine, diethylamine, and pyridine.

When component (b) is an organosilicon compound in which E is an amino group or a substituted amino group, A in component (a) is limited to the hydrogen atom. This reaction will run in the absence of catalyst, but a small amount of an acidic compound such as trifluoroacetic acid, trimethylchlorosilane, or ammonium chloride, can also be added as catalyst to accelerate the reaction rate.

When component (a) is a mixture that contains both hydrogen and alkali metal atoms for different instances of A, and component (b) is an organosilicon compound in which E is an acyloxy group, an amine compound is preferably added as a carboxylic acid scavenger to inhibit equilibration reactions by the organopolysiloxane chain under the influence of the carboxylic acid by-product generated by this reagent combination. These amine compounds are exemplified by triethylamine, diethylamine, and pyridine.

This invention further relates to an alternative method for preparing the macromonomer having the formula

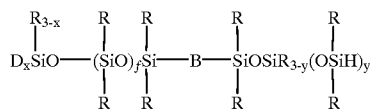

wherein D, R, B, x, f and y are as described above. This method comprises (I') reacting component (a') which has the general formula

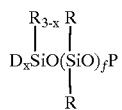

where D, R, and f are as defined above, and P is selected from the group consisting of halogen atoms and alkali metal atoms; and component (b'), which has the general formula

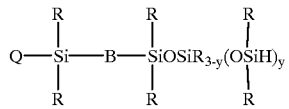

where R, B, and y are as defined above and Q is selected from the group consisting of alkali metal atoms and halogen atoms; with the provisos that when P is an alkali metal atom, Q is a halogen atom; and when Q is an alkali metal atom, P is a halogen atom. The halogen atom is preferably chlorine, and the alkali metal atom is preferably lithium.

Preferably, component (a') has formula $Li(OSiR_2)_f$—$CH{=}CH_2$ and component (a') is formed by reacting $CH_2{=}CHSiR_2OLi$ with $(R_2SiO)_3$ in proportions predetermined to obtain the desired value of f described above.

In a preferred embodiment, and component (a') has the formula $Li(OSiR_2)_f$—$CH{=}CH_2$, and component (b') is a compound of the formula:

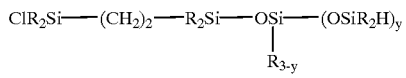

In a particularly preferred embodiment, y=2 and component (b') has formula $(HSiR_2O)_2Si(R)$—$SiR_2$—$(CH_2)_2$—$SiR_2Cl$, wherein component (b') is formed by reacting $(HSiR_2O)_3SiR$ with $CH_2{=}CHSiR_2Cl$ in the presence of a platinum catalyst.

The catalyst comprising a group VIII metal which may be employed in the preparation of the macromonomer, and also in the polymerization of the macromonomer, is any such catalyst suitable for use in hydrosilylation reactions. Examples of suitable catalysts are ruthenium, rhodium, palladium, osmium, iridium and platinum. Preferably the catalyst is a platinum compound or complex. Suitable platinum compounds and complexes include chloroplatinic acid, platinum acetylacetonate, complexes of platinous halides with unsaturated compounds such as ethylene, propylene, organovinylsiloxanes, and styrene, hexamethyldiplatinum, $PtCl_2$, $PtCl_3$, $PtCl_4$, and $Pt(CN)_3$.

This invention further relates to a method for preparing a hyperbranched polymer by polymerizing a macromonomer having one or more aliphatically unsaturated organic groups at one molecular chain terminal and one or more silicon bonded hydrogen atoms at the other molecular chain terminal with a group VIII metal catalyst, e.g. platinum, catalysts. Suitable group VIII metal catalysts are disclosed above.

For macromonomers having a single aliphatically unsaturated group D and two or three SiH groups, 100% conversion of the aliphatically unsaturated groups can be achieved after several hours. The molecular masses of the reaction products depend on several factors, particularly the type of macromonomer and the concentration of macromonomer and catalyst in solution.

Macromonomers having a single aliphatically unsaturated group D and two or three SiH groups, will polymerize to form a hyperbranched polymer with an SiH surface. When the hyperbranched polymer has an SiH surface, it can be stabilized by addition of a volatile SiH-containing compound or by extracting platinum-containing compounds using an immiscible nitrogen-containing polar solvent. The volatile SiH-containing compound may be trimethylsilane or tetramethyldisiloxane. The solvent may be tetramethylethylenediamine, polyethylenepolyamine or acetonitrile.

This invention further relates to a method for stabilizing the hyperbranched polymers. To stabilize the hyperbranched polymers, control is preferably effected over catalyst concentration minimization and reaction mixture dilution. On completion of reaction, the Group VIII metal, e.g. platinum, catalyst is preferably deactivated or a low molecular weight SiH compound is added.

EXAMPLES

These examples are intended to illustrate the invention to those skilled in the art and should not be interpreted as limiting the scope of the invention set forth in the claims.

Reference Example 1

265.7 g methyltris(dimethylvinylsiloxy)silane and sufficient platinum/1,3-divinyltetramethyldisiloxane complex to provide 5 ppm platinum metal based on the total weight of the reaction mixture were introduced into a stirrer-equipped four-neck flask. After heating to 90° C., 50.8 g dimethylchlorosilane was added dropwise and the reaction was then stirred for 1 hour at 90 to 100° C. Analysis of the resulting reaction mixture by gas chromatography (GLC) showed that the peak for the dimethylchlorosilane had disappeared, which indicated that the reaction was complete. During distillation in vacuo, the fraction boiling at 90–107° C./5 mmHg was discarded and the fraction boiling at 130–133° C./2 mmHg was recovered to afford 112.0 g reaction product.

The recovered compound was confirmed by infrared absorption analysis (IR) and GLC analysis to be the chlorosilethylenesiloxane compound with the following formula in a yield of 47.3%.

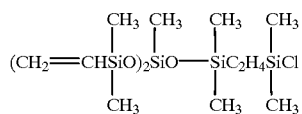

Reference Example 2

31.8 g sodium acetate and 100 mL toluene were placed in a stirrer-equipped four-neck flask and heated to carry out azeotropic drying. 86.2 g of the chlorosilethylenesiloxane compound prepared in Reference Example 1 was then added at 60° C., after which the temperature was raised to 90° C., and the reaction was stirred for 135 minutes. The reaction was regarded as complete after this stirring from the fact that the liquid in the reaction mixture had changed from acidic to neutral. 100 mL water was added to the reaction mixture, and separatory extraction then gave the reaction product as the toluene solution.

The obtained compound was confirmed by GLC analysis to be the acetoxysilethylenesiloxane with the following formula in a purity of 99.5%.

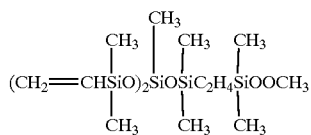

Reference Example 3

An aqueous solution was prepared by the introduction of 34.8 g sodium bicarbonate and 100 mL water into a stirrer-equipped four-neck flask. Thereafter, the toluene solution of acetoxysilethylenesiloxane prepared in Reference Example 2 was added, and then 5 mL diethylamine. After heating to 40° C. the reaction was stirred for 150 minutes. GLC analysis of the reaction mixture after stirring showed that the peak for the starting acetoxysilethylenesiloxane had disappeared, which indicated that the reaction was complete. The reaction mixture was subjected to separatory extraction, washing with water, and distillation of the solvent to give 79.5 g reaction product.

The compound thus obtained was confirmed by GLC analysis to be the siloxanol compound with the following formula in a purity of 98.0% in a yield of 96.3%.

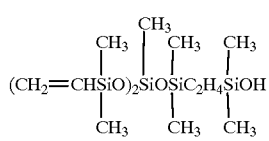

Example 1

270.1 g hexamethylcyclotrisiloxane and 310 mL toluene were placed in a stirrer-equipped four-neck flask and heated in order to carry out azeotropic drying. 43.7 g of the siloxanol compound prepared in Reference Example 3 was placed in a separate stirrer-equipped four-neck flask, and, while cooling this reaction system with ice water, 0.7 mL of a 1.54 mol/L n-hexane solution of n-butyllithium was added while stirring. The previously dried toluene solution of hexamethylcyclotrisiloxane was added to this reaction system followed by the addition of 20.0 g acetonitrile and 20.0 g dimethylformamide. The reaction system was then stirred for 170 minutes at 30° C. GLC analysis of the reaction mixture after stirring gave a hexamethylcyclotrisiloxane conversion of 77%, on the basis of which the reaction was regarded as finished. The reaction was then stopped by the addition of 0.7 mL acetic acid. After stirring overnight at room temperature, the solvent was distilled off and the precipitated salt by-product was removed by sterilizing filtration to give 253.3 g polymer.

This polymer was confirmed by nuclear magnetic resonance spectroscopic analysis (NMR) to be the macromonomer with the following formula in a yield of 97.5%.

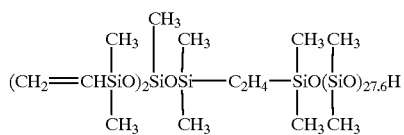

Example 2

301.1 g hexamethylcyclotrisiloxane and 310 mL toluene were placed in a stirrer-equipped four-neck flask and heated in order to carry out azeotropic drying. 34.1 g of the siloxanol compound prepared in Reference Example 3 was placed in a separate stirrer-equipped four-neck flask, and, while cooling this reaction system with ice water, 0.7 mL of a 1.54 mol/L n-hexane solution of n-butyllithium was added while stirring. The previously dried toluene solution of hexamethylcyclotrisiloxane was added to this reaction system followed by the addition of 20.0 g acetonitrile and 20.0 g dimethylformamide. The reaction system was then stirred for 170 minutes at 30° C. GLC analysis of the reaction mixture after stirring gave a hexamethylcyclotrisiloxane conversion of 77%, on the basis of which the reaction was regarded as finished. The reaction was then stopped by the addition of 0.7 mL acetic acid. After stirring overnight at room temperature, the solvent was distilled off and the precipitated salt by-product was removed by sterilizing filtration to give 253.3 g polymer.

This polymer was confirmed by NMR to be the macromonomer with the following formula in a yield of 95.2%.

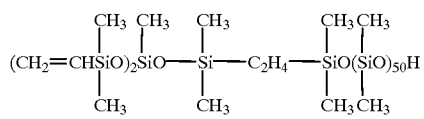

Example 3

297.2 g hexamethylcyclotrisiloxane and 310 mL toluene were placed in a stirrer-equipped four-neck flask and heated in order to carry out azeotropic drying. 17.0 g of the siloxanol compound prepared in Reference Example 3 was placed in a separate stirrer-equipped four-neck flask, and, while cooling this reaction system with ice water, 0.3 mL of a 1.54 mol/L n-hexane solution of n-butyllithium was added while stirring. The previously dried toluene solution of hexamethylcyclotrisiloxane was added to this reaction system followed by the addition of 20.0 g acetonitrile and 20.0 g dimethylformamide. The reaction system was then stirred for 170 minutes at 30° C. GLC analysis of the reaction mixture after stirring gave a hexamethylcyclotrisiloxane conversion of 81%, on the basis of which the reaction was regarded as finished. The reaction was then stopped by the addition of 0.7 mL acetic acid. After stirring overnight at room temperature, the solvent was distilled off and the precipitated salt by-product was removed by sterilizing filtration to give 246.0 g polymer.

This polymer was confirmed by NMR to be the macromonomer with the following formula in a yield of 95.4%.

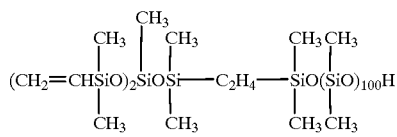

Example 4

50.6 g of the macromonomer produced in Example 1 and 100 mL toluene were placed in a stirrer-equipped four-neck flask and heated in order to carry out azeotropic drying. 3.6 g triethylamine was then added to the solution at room temperature, followed by the dropwise addition of 3.5 g vinyldimethylchlorosilane. After stirring overnight at room temperature, 10 mL methanol was added followed by stirring for an additional 60 minutes at room temperature. The solvent was subsequently distilled off and the precipitated salt by-product was removed by sterilizing filtration to give 47.0 g polymer.

This polymer was confirmed by NMR to be the macromonomer with the following formula in a yield of 90.0%.

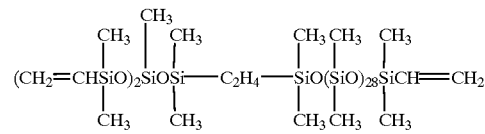

Example 5

307.8 g hexamethylcyclotrisiloxane and 350 mL toluene were placed in a stirrer-equipped four-neck flask and heated in order to carry out azeotropic drying. 168.7 g of the siloxanol compound prepared in Reference Example 3 was placed in a separate stirrer-equipped four-neck flask, and, while cooling this reaction system with ice water, 3.0 mL of a 1.68 mol/L n-hexane solution of n-butyllithium was added while stirring. The previously dried toluene solution of hexamethylcyclotrisiloxane was added to this reaction system followed by the addition of 20.0 g acetonitrile and 20.0 g dimethylformamide. The reaction system was then stirred for 190 minutes at 30° C. GLC analysis of the reaction mixture after stirring gave a hexamethylcyclotrisiloxane conversion of 81%, on the basis of which the reaction was regarded as finished. The reaction was subsequently stopped by the addition of 41.5 g diethylamine and then 47.3 g dimethylchlorosilane. After stirring overnight at room temperature, 30 mL methanol was added followed by stirring for an additional 60 minutes. The solvent was then distilled off and the precipitated salt by-product was removed by sterilizing filtration to give 433.1 g polymer.

This polymer was confirmed by NMR to be the macromonomer with the following formula in a yield of 98.0%.

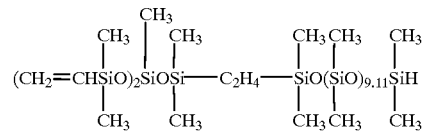

Example 6

300.9 g hexamethylcyclotrisiloxane and 350 mL toluene were placed in a stirrer-equipped four-neck flask and heated in order to carry out azeotropic drying. 168.7 g of the siloxanol compound prepared in Reference Example 3 was placed in a separate stirrer-equipped four-neck flask, and, while cooling this reaction system with ice water, 3.0 mL of a 1.68 mol/L n-hexane solution of n-butyllithium was added while stirring. The previously dried toluene solution of hexamethylcyclotrisiloxane was added to this reaction system followed by the addition of 20.0 g acetonitrile and 20.0 g dimethylformamide. The reaction system was then stirred for 300 minutes at 30° C. GLC analysis of the reaction mixture after stirring gave a hexamethylcyclotrisiloxane conversion of 81%, on the basis of which the reaction was regarded as finished. The reaction was subsequently stopped by the addition of 7.8 g diethylamine and then 9.5 g dimethylchlorosilane. After stirring overnight at room temperature, 20 mL methanol was added followed by stirring for an additional 60 minutes. The solvent was then distilled off and the precipitated salt by-product was removed by sterilizing filtration to give 255.6 g polymer.

This polymer was confirmed by NMR to be the macromonomer with the following formula in a yield of 92.0%.

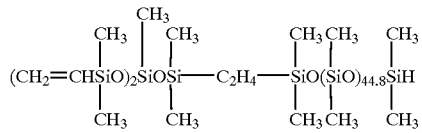

Example 7

297.2 g hexamethylcyclotrisiloxane and 350 mL toluene were placed in a stirrer-equipped four-neck flask and heated in order to carry out azeotropic drying. 17.0 g of the siloxanol compound prepared in Reference Example 3 was placed in a separate stirrer-equipped four-neck flask, and, while cooling this reaction system with ice water, 0.3 mL of a 1.68 mol/L n-hexane solution of n-butyllithium was added while stirring. The previously dried toluene solution of hexamethylcyclotrisiloxane was added to this reaction system followed by the addition of 20.0 g acetonitrile and 20.0 g dimethylformamide. The reaction system was then stirred for 180 minutes at 30° C. GLC analysis of the reaction mixture after stirring gave a hexamethylcyclotrisiloxane conversion of 81%, on the basis of which the reaction was regarded as finished. The reaction was subsequently stopped by the addition of 3.7 g diethylamine and then 4.7 g dimethylchlorosilane. After stirring overnight at room temperature, 20 mL methanol was added followed by stirring for an additional 60 minutes. The solvent was then distilled off and the precipitated salt by-product was removed by sterilizing filtration to give 255.6 g polymer.

This polymer was confirmed by NMR to be the macromonomer with the following formula in a yield of 95.4%.

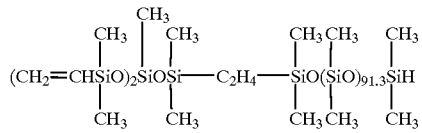

Example 8

50.6 g of the macromonomer produced in Example 1 and 100 mL toluene were placed in a stirrer-equipped four-neck flask and heated in order to carry out azeotropic drying. 2.8 g diethylamine was then added to the solution at room temperature, followed by the dropwise addition of 6.4 g methacryloxypropyldimethylchlorosilane. After stirring overnight at room temperature, 10 mL methanol was added followed by stirring for an additional 60 minutes at room temperature. The solvent was subsequently distilled off and the precipitated salt by-product was removed by sterilizing filtration to give 47.0 g polymer.

This polymer was confirmed by NMR to be the macromonomer with the following formula in a yield of 88.3%.

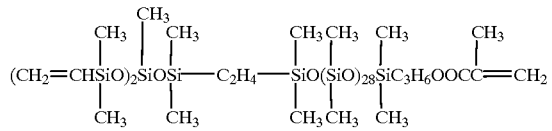

Example 9

50.6 g of the macromonomer produced in Example 1 and 100 mL toluene were placed in a stirrer-equipped four-neck flask and heated in order to carry out azeotropic drying. 4.2 g 1,2,2,4-tetramethyl-1-aza-2-silacyclopentane was then added dropwise to this solution at room temperature. After stirring overnight at room temperature, the solvent was distilled off and the precipitated salt by-product was removed by sterilizing filtration to give 47.0 g polymer.

This polymer was confirmed by NMR to be the macromonomer with the following formula in a yield of 88.7%.

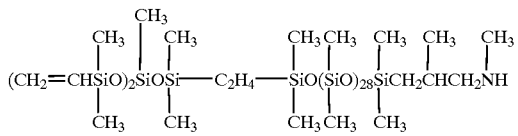

Example 10

5.4 g of the macromonomer prepared in Example 5, 0.6 g 1-hexene, and sufficient platinum/1,3-divinyltetramethyldisiloxane complex to provide 10 ppm platinum metal based on the total weight of the reaction mixture were introduced into a stirrer-equipped four-neck flask and heated to 70° C. After the flask had been stirred for 30 minutes, the reaction mixture was analyzed by IR. It was found that the absorption at 2150 cm$^{-1}$ assigned to the silicon-hydrogen bond had disappeared and the reaction was therefore regarded as completed. The reaction product was recovered by removal of the low boilers by heating under reduced pressure.

Measurement of the molecular weight of the obtained reaction product by gel permeation chromatography (GPC) using polystyrene standards confirmed it to be a highly branched polysiloxane (hyperbranched polymer) with a number-average molecular weight of $9.23 \times 10^3$ and a weight-average molecular weight of $1.98 \times 10^4$. This hyperbranched polymer had a dispersity of 2.15. This polymer was stored for 2 months at room temperature and its molecular weight was then measured by the same method as before, and no significant changes in either molecular weight or dispersity were observed.

Example 10 shows that the storage stability of hyperbranched polymers made by addition reaction of a macromonomer having one silicon bonded hydrogen atom at one molecular chain terminal and more than one aliphatically unsaturated organic group at the other molecular chain terminal is good.

Comparative Example 1

For purposes of comparison, 5.4 g of the organopolysiloxane-type polymer with the following formula:

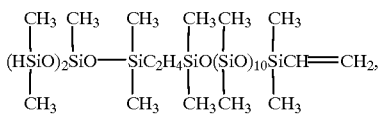

2.6 g 1,1,3,3,5,5,7,7,9,9-decamethylpentasiloxane, and sufficient platinum/1,3-divinyltetramethyldisiloxane complex to provide 10 ppm platinum metal based on the total weight of the reaction mixture were introduced into a stirrer-equipped four-neck flask and heated to 70° C. After the flask had been stirred for 120 minutes, the reaction mixture was analyzed by IR. It was found that the absorption at 1600 cm$^{-1}$ assigned to the vinyl group had disappeared and the reaction was therefore regarded as completed. The reaction product was recovered by removal of the low boilers by heating under reduced pressure.

Measurement of the molecular weight of the obtained reaction product by gel permeation chromatography (GPC) using polystyrene standards confirmed it to be a hyperbranched polymer with a number-average molecular weight of $5.77 \times 10^3$ and a weight-average molecular weight of $8.89 \times 10^3$. This polymer had a dispersity of 1.54. This polymer was stored for 2 months at room temperature and its molecular weight was then measured by the same method as before. Timewise changes were seen in this case as the number-average molecular weight had increased to $6.80 \times 10^3$, the weight-average molecular weight had increased to $1.23 \times 10^4$, and the dispersity had also increased to 1.80.

Comparative Example 1 shows that storage stability of hyperbranched polymers made by addition reaction of a macromonomer having one aliphatically unsaturated organic group at one molecular chain terminal and more than one silicon bonded hydrogen atom at the other molecular chain terminal is poor without further treatment to stabilize the hyperbranched polymer.

In the following examples, macromonomers having a single aliphatically unsaturated group at one molecular chain terminal and 2 or 3 SiH groups at the other molecular chain terminal were synthesized. For macromonomers having a single aliphatically unsaturated group D and two or three SiH groups, 100% conversion of the aliphatically unsaturated groups can be achieved after several hours. The molecular masses of the reaction products depend on several factors, particularly the type of macromonomer and the concentration of macromonomer and catalyst in solution. In the case of a relatively small macromonomer, such as MM-1 in the examples below, experiments with a 50% solution of the macromonomer in n-hexane show full conversion of vinyl groups and 50% conversion of SiH groups, and the molecular mass of the product coincides with the molecular mass of the macromonomer. This can be explained by a cyclization process only. In bulk, a soluble polymer with a molecular mass range of 15,000 to 30,000 was obtained.

With larger macromonomers (such as MM-2 and MM-3 in the examples below) reactions in bulk may lead to obtaining crosslinked insoluble products. In the case of polymerization in solution, both these macromonomers after full conversion of vinyl groups gave soluble polymers. The most probable side reaction, leading to crosslinking, is interaction of functional groups with platinum catalyst with subsequent regrouping. Decreasing the catalyst concentration allows for obtaining fully soluble products at total conversion of vinyl groups.

Hyperbranched H-functional hyperbranched polydimethylsiloxanes and similar products based on the macromonomers of this invention. The obtained hyperbranched polymers are transparent slow-moving liquids. The intrinsic viscosity of the obtained hyperbranchedpolymers varies from 0.15 to 0.65 dl/g and molecular masses of from 15,000 to 800,000, depending on the size of the initial macromonomer.

Example 11

Hydrogen functional trisiloxymethylsilane was reacted with vinylchlorodimethylsilane in toluene in the presence of a platinum catalyst in accordance with the following equation to produce the intermediate (I):

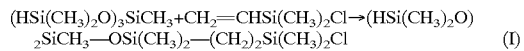

Lithiumvinylsilanoate was reacted with cyclic trisiloxane in a solvent mixture of 96 % toluene and 4% dimethylformamide to form the intermediate (II) in accordance with the following equation:

The value of f in the intermediate (II) is controlled by the ratio of amounts of reagents in this step. The intermediates (I) (103 mmol) and (II) (85 mmol) are then reacted together in 220 g of a mixture of 96% toluene and 4% dimethylformamide with elimination of lithiumchloride over a period of 15 hours in accordance with the following equation:

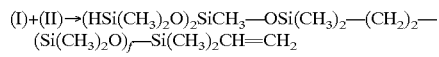

Three macromonomers were prepared with properties as set out in Table 1 below:

TABLE 1

| | Macromonomers parameters | | | | |
|---|---|---|---|---|---|
| Macromonomer | f | $M_{calk}$ | $M_{GPC}$ | $M_w/M_n$ | $M_{PMR}$ |
| MM-1 | 10 | 1046 | 1120 | 1.16 | 1192 |
| MM-2 | 50 | 4006 | 4310 | 1.07 | 5480 |
| MM-3 | 100 | 7706 | 7720 | 1.03 | 7940 |

The macromonomers were analyzed by IR and NMR spectroscopy and by GPC.

The samples had a narrow molecular mass distribution and a good relation between calculated and experimental data for molecular mass.

Example 12

Polyaddition of Macromonomer in Bulk

To 20 g ($2.10^{-2}$ mol) of macromonomer MM-1 in a flask under argon was added 10 ml of solution of Pt-catalyst PC072 ($1.5.10^{-3}$% mass Pt) via a syringe. The reaction was followed by taking of probes for $^1$H NMR. In 24 hours at room temperature the reaction ended. GPC: monomodal molar mass distribution. After precipitation of 5% hexane solution by ethanol 80% mass of polymer was obtained with MM about 15000.

Example 13

Polyaddition of Macromonomer in Solution

To 30% hexane solution of macromonomer MM-2 20 g ($5.10^{-3}$ mol) under argon was added 10 ml of solution of Pt-catalyst PC072 ($2.10^{-3}$% mass Pt) via a syringe. In 24 hours at room temperature the reaction was over by the data of $^1$H NMR-spectra. GPC: monomodal molar mass distribution with maximum of curve about 35000.

Following the procedures of Examples 12 and 13 above, further polyaddition processes were carried with the results shown in Table 2 below:

TABLE 2

Results of polyaddition processes (TMBDA is tetramethylethylenediamine. PEPA is polyethylenepolyamine.)

| Ex | Macromonomer concentration mass % | Cat., mass % | Time of reaction h | Conversion of vinyl groups, % | Mole mass by GPC data | Intrinsic viscosity [O], dl/g | life time, h |
|---|---|---|---|---|---|---|---|
| 14 | MM-1 25 | Pt2*10$^{-3}$ | 48 | 100 | 1000 | 0.085 | " |
| 15 | " | " | 72 | 100 | 1000 | — | " |
| 16 | MM-1 bulk | " | 72 | 100 | 15000 | — | " |
| 17 | " | 1.5*10$^{-3}$ | 24 | 100 | 15000 | — | " |
| 18 | MM-1 33 | 1.5*10$^{-3}$ | 240 | 100 | 1000 | — | " |
| 19 | MM-2 25 | Pt 2*10$^{-3}$ | 48 | 100 | 35000 | 0.48 | ~200 |
| 20 | MM-2 30 | 2*10$^{-4}$ | 96 | 0 | — | — | — |
| 21 | MM-2 bulk | 2*10$^{-4}$ | 72 | 100 | gel | — | — |
| 22 | MM-2 bulk | 2*10$^{-4}$ | 24, with adding HSiMe$_3$ | 100 | 10000 | — | no gel |
| 23 | MM-2 34 | 1.5*10$^{-3}$ | 48 | 100 | 3500 | — | ~200 |
| 24 | " | " | 48, with adding HSiMe$_3$ | " | " | — | no gel |
| 25 | MM-2 30 | 2*10$^{-4}$ | 72 | 100 | 12000 | 0.19 | ~300 |
| 26 | MM-2 bulk | 1.5*10$^{-3}$ | 24 | 100 | gel | — | — |
| 27 | MM-3 bulk | Pt2*10$^{-3}$ | 24 | 100 | gel | — | — |
| 28 | " | 2*10$^{-4}$ | 24 | 100 | gel | — | — |
| 29 | MM-3 30 | 2*10$^{-3}$ | 48 | 100 | 80000 | 0.64 | 100 |
| 30 | MM-3 5 | 3*10$^{-3}$ | 48 | 100 | " | — | ~1000 in solution |
| 31 | MM-3 10 | " | 48 | 100 | " | — | 200 |
| 32 | MM-3 25 | " | 48 | 100 | " | — | 100 |
| 33 | MM-3 3 | 1.5*10$^{-3}$ | 48 | 100 | 80000 | — | no gel in solution |
| 34 | MM-3 3 | 0.6*10$^{-3}$ | 48 | 100 | 80000 | — | no gel in solution |
| 35 | MM-3 28 | 1.5*10$^{-3}$ | 48 | 100 | " | — | ~100 |
| 36 | MM-3 28 | 1.5*10$^{-3}$ | 48, with adding HSiMe$_3$ | 100 | " | — | no gel |
| 37 | MM-3 28 | 1.5*10$^{-3}$ | 48, with washing by TMEDA | 100 | " | — | no gel |
| 38 | MM-3 28 | 1.5*10$^{-3}$ | 48, with washing by PEPA | 100 | " | — | no gel |
| 39 | MM-3 30 | 3*10$^{-4}$ | 48 | 100 | 70000 | 0.64 | 100 |

We claim:

1. A macromonomer having the general formula:

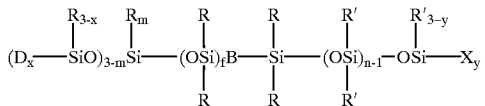

wherein each D is independently an aliphatically unsaturated organic group, each R is independently selected from the group consisting of monovalent hydrocarbon groups free of aliphatic unsaturation and monovalent halogenated hydrocarbon groups free of aliphatic unsaturation; each R' is independently selected from the group consisting of monovalent hydrocarbon groups and monovalent halogenated hydrocarbon groups, B is selected from the group consisting of an oxygen atom and a divalent hydrocarbon group having at least two carbon atoms and free of aliphatic unsaturation; each X is independently selected from the group consisting of hydroxyl groups, monovalent organosiloxy-groups containing a silicon-bonded functionality selected from the group consisting of a hydrogen atom, alkenyl groups, acryloxy groups, methacryloxy groups, vinylphenyl groups, primary amino groups, and secondary amino groups, and groups of the formula

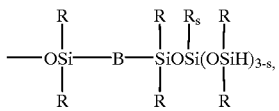

wherein s is 0 or 1; n is an integer with a value of 1 to 1,001; x is 1, 2, or 3; m is 0, 1, or 2; f is an integer with a value greater than or equal to 0; and y is 1, 2, or 3.

2. The macromonomer of claim 1, wherein each R and each R' are independently selected from the group consisting of alkyl, haloalkyl, and aryl groups.

3. The macromonomer of claim 2, wherein each R and each R' are methyl.

4. The macromonomer of claim 1, wherein D is selected from the group consisting of alkenyl-containing groups and alkynyl-containing groups.

5. The macromonomer of claim 4, wherein D is selected from the group consisting of lower alkenyl groups and alkynyl groups of 2 to 6 carbon atoms.

6. The macromonomer of claim 5, wherein D is selected from the group consisting of vinyl and allyl, with the proviso that the unsaturation of the allyl group is terminal.

7. The macromonomer of claim 1, wherein B is a divalent hydrocarbon group of at least 2 carbon atoms free of aliphatic unsaturation.

8. The macromonomer of claim 7, wherein B is selected from the group consisting of ethylene, methylmethylene, propylene, butylene, and hexylene.

9. The macromonomer of claim 1, wherein f is 1 and x is 1, whereby the macromonomer has the formula:

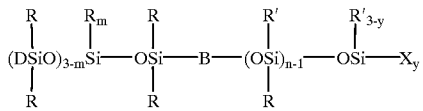

wherein D is an aliphatically unsaturated organic group, each R is independently a monovalent hydrocarbon group free of aliphatic unsaturation, each R' is a monovalent hydrocarbon group, B is a divalent hydrocarbon group with at least 2 carbon atoms and free of aliphatic unsaturation n is 1 to 1,001, y is 1, 2, or 3, m is 0 or 1, and X is selected from the group consisting of a hydroxyl group and a monovalent organosiloxy group.

10. The macromonomer of claim 9, wherein D is a vinyl group, R is a methyl group, B is selected from the group consisting of ethylene, methylethylene, butylene, and hexylene, and n is 1 to 501.

11. The macromonomer of claim 9, wherein the monovalent organosiloxy group for X is selected from the group consisting of —OSi(R$_2$)Z and

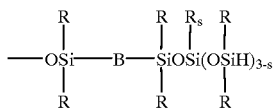

wherein R and B are as defined above, Z is selected from the group consisting of hydrogen, alkenyl groups, acryloxy groups, methacryloxy groups, vinylphenyl groups, primary amino groups, and secondary amino groups, and s is 0 or 1.

12. The macromonomer of claim 1, wherein m is 2, n is 1, R' is R, X is —OSi(R$_2$)Z, and Z is a hydrogen atom, whereby the macromonomer has the formula

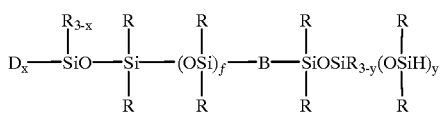

wherein D, R, f and B are as described above; x is 1, 2, or 3; y is 1, 2, or 3; with the provisos that when x is 1, y is 2 or 3 and when y is 1, x is 2 or 3.

13. The macromonomer of claim 12, wherein each R is independently selected from the group consisting of alkyl groups of 1 to 6 carbon atoms, haloalkyl groups of 1 to 6 carbon atoms, and phenyl groups; and f is 10 to 100.

14. The macromonomer of claim 12, wherein the macromonomer has formula:

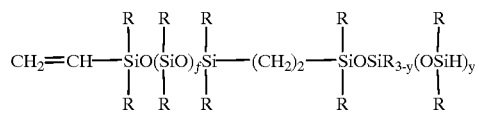

wherein R and f are as described above, and y is 2 or 3.

15. The macromonomer of claim 14, wherein the macromonomer has the formula:

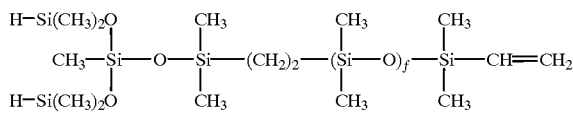

wherein f has a value of 10 to 100.

16. A method for synthesizing a macromonomer, wherein the method comprises:

(1) effecting the ring-opening polymerization of component (C) a cyclic trisiloxane, using component (A) a lithium siloxanolate as polymerization initiator, and (2) terminating the ring-opening polymerization with component (D) a terminating agent; wherein component (A) has the formula

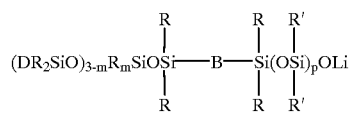

wherein D is an aliphatically unsaturated organic group; each R is independently a monovalent hydrocarbon group free of aliphatic unsaturation; each R' is independently a monovalent hydrocarbon group; B is a divalent hydrocarbon group having at least two carbon atoms and free of aliphatic unsaturation; m is 0 or 1; and p is an integer with a value no greater than 10, component (C) has the general formula

wherein R' is as described above, and component (D) is selected from the group consisting of acids, and halosilyl functional compounds.

17. A method for synthesizing a macromonomer, wherein the method comprises (1) effecting ring-opening polymerization of component (C) a cyclic trisiloxane using component (A) a polymerization initiator (2) terminating the ring-opening polymerization with component (D) an acid terminating agent, thereby synthesizing an organopolysiloxane-type polymer in which one molecular chain terminal is blocked by aliphatically unsaturated bond-containing organic groups and the other terminal is blocked by silanol, having the formula

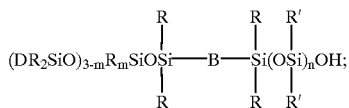

and thereafter
  (3) reacting the organopolysiloxane-type polymer with component (E), wherein (E) is selected from the group consisting of: an amine compound and a hydrolyzable compound; wherein
  component (A) is a lithium siloxanolate with the general formula

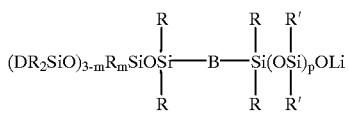

wherein each D is independently an aliphatically unsaturated organic group; each R is independently selected from monovalent hydrocarbon groups free of aliphatic unsaturation; each R' is independently selected from monovalent hydrocarbon groups; B is a divalent hydrocarbon group having at least two carbon atoms and free of aliphatic unsaturation; m is 0 or 1; n is an integer with a value from 1 to 1,000 that is larger than p, and p is an integer with a value no greater than 10,
  component (C) is a cyclic trisiloxane with the general formula

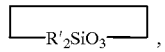

wherein R' is as described above,
  component (D) is a terminating agent selected from the group consisting of acids,
  the amine compound for component (E) is selected from the group consisting of a cyclic silylamine, and an N-substituted cyclic silylamine, and
  the hydrolyzable compound for component (E) is selected from the group consisting of an SiH-functional compound that contains a hydrolyzable silyl group, an alkenyl-functional compound that contains a hydrolyzable silyl group, an acryloxy-functional compound that contains a hydrolyzable silyl group, a methacryloxy-functional compound that contains a hydrolyzable silyl group, and a compound that contains both a vinylphenyl group and a hydrolyzable silyl group.

18. The method of claim 16 or 17, wherein component (B) a molecular weight regulator is added in step (1), wherein component (B) is an organosiloxanol with the general formula

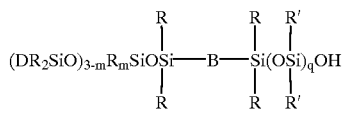

wherein D, m, R, B, and R' are as described above and q is an integer with a value no greater than 10.

19. The method of claim 16 or 17, wherein component (C) is selected from the group consisting of

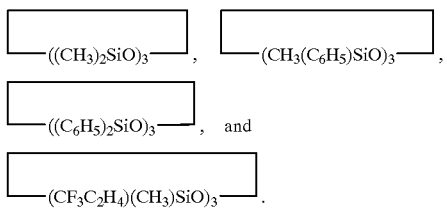

20. The method of claim 16 or 17, wherein the cyclic trisiloxane takes the form of a solid and an aprotic organic solvent is used, thereby allowing reaction in a homogeneous system.

21. The method of claim 16 or 17, wherein synthesis is carried out at a temperature in the range of 0 to 100° C.

22. The method of claim 16 or 17, wherein component (D) is an acid selected from the group consisting of wet carbon dioxide, mineral acids, and organic acids.

23. The method of claim 16, wherein component (D) is a halosilyl functional compound selected from the group consisting of SiH-functional compounds that contain a halosilyl group, alkenyl-functional compounds that contain a halosilyl group, acryloxy-functional compounds that contain a halosilyl group, methacryloxy-functional compounds that contain a halosilyl group, and compounds that contain both a vinylphenyl group and a halosilyl group.

24. The method of claim 23, wherein a hydrogen halide scavenger selected from the group consisting of an organic amine compound and ammonia is added.

25. A method for synthesizing a macromonomer comprising:
  (i) reacting components (a) and (b) to form a product; wherein
  component (a) has the formula

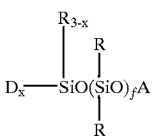

wherein D is an aliphatically unsaturated organic group, each R is independently selected from the group consisting of monovalent hydrocarbon groups free of aliphatic unsaturation and monovalent halogenated hydrocarbon groups free of aliphatic unsaturation; f is an integer with a value greater than or equal to 0; x is 1, 2, or 3; and A is selected from the group consisting of a hydrogen atom, an alkali metal atom, and combinations thereof; and
  component (b) has formula

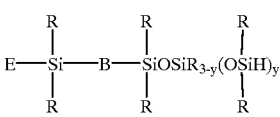

where R is as defined above; B is selected from the group consisting of an oxygen atom and a divalent hydrocarbon group with at least 2 carbon atoms and free of aliphatic unsaturation; E is selected from the group consisting of halogen atoms, amino groups, substituted amino groups, and acyloxy groups; y is 1, 2, or 3; with the provisos that when x is 1, y is 2 or 3 and when y is 1, x is 2 or 3; and when E is an amino group or a substituted amino group, A is hydrogen.

26. The method of claim 25, wherein when component (a) is a mixture comprising both hydrogen and alkali metal atoms for different instances of A and E is a halogen atom, and the method further comprises adding an amine compound to the product of step (i).

27. The method of claim 26, wherein the amine compound is selected from the group consisting of triethylamine, diethylamine, and pyridine.

28. The method of claim 25, wherein when E is an amino group or a substituted amino group and A is hydrogen, the method further comprises adding a small amount of an acidic compound to components (a) and (b).

29. The method of claim 28, wherein the acidic compound is selected from the group consisting of trifluoroacetic acid, trimethylchlorosilane, and ammonium chloride.

30. The method of claim 25, wherein when component (a) is a mixture comprising both hydrogen and alkali metal atoms for different instance of A and E is an acyloxy group, the method further comprises adding an amine compound to the product of step (i).

31. The method of claim 30, wherein the amine compound is selected from the group consisting of triethylamine, diethylamine, and pyridine.

32. The method of claim 25, wherein E is selected from the group consisting of a chlorine atom and a diethylamino group.

33. The method of claim 32, wherein E is a chlorine atom.

34. The method of claim 25, wherein component (b) has the formula

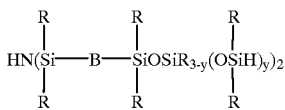

wherein R, B, and y are as described above.

35. The method of claim 25, wherein at least 1 equivalent of component (b) based on component (a) is present.

36. The method of claim 35, wherein there is at least 1.05 equivalent of component (b) based on component (a).

37. The method of claim 25, wherein reacting components (a) and (b) is carried out in the presence of an organic solvent.

38. The method of claim 25, wherein reacting components (a) and (b) is carried out at 0 to 200° C.

39. The method of claim 38, where reacting components (a) and (b) is carried out at 20 to 100° C.

40. A method of preparing a macromonomer, wherein the method comprises (I') reacting components (a') and (b'); wherein component (a') has general formula

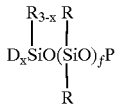

wherein D is an aliphatically unsaturated organic group, each R is independently selected from the group consisting of monovalent hydrocarbon groups free of aliphatic unsaturation and monovalent halogenated hydrocarbon groups free of aliphatic unsaturation; n is an integer with a value greater than or equal to 0; x is 1, 2, or 3; and P is selected from the group consisting of halogen atoms and alkali metal atoms; and component (b') has general formula

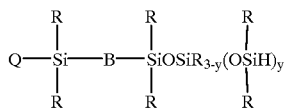

where R, is as defined above; B is selected from the group consisting of an oxygen atom and a divalent hydrocarbon group with at least 2 carbon atoms and free of aliphatic unsaturation; y is 1, 2, or 3, Q is selected from the group consisting of alkali metal atoms and halogen atoms; with the provisos that when x is 1, y is 2 or 3; when y is 1, x is 2 or 3; when P is an alkali metal atom, Q is a halogen atom; and when Q is an alkali metal atom, P is a halogen atom.

41. The method of claim 40, wherein component (a') has the formula $Li(OSiR_2)_f CH=CH_2$, wherein f is 0 to 1,000; and component (b') has the formula $(HSiR_2O)_y SiOR_{3-y} OSiR_2(CH_2)_2 SiR_2 Cl$, wherein y is 2 or 3.

42. A method of forming a hyperbranched polymer, wherein the method comprises polymerizing a macromonomer with a catalyst comprising a group VIII metal; wherein the macromonomer has the formula

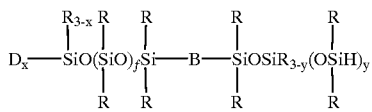

wherein each D is independently an aliphatically unsaturated organic group, each R is independently selected from the group consisting of monovalent hydrocarbon groups free of aliphatic unsaturation and monovalent halogenated hydrocarbon groups free of aliphatic unsaturation; B is selected from the group consisting of an oxygen atom and a divalent hydrocarbon group of at least two carbon atoms and free of aliphatic unsaturation; f is an integer with a value greater than or equal to 0; x is 1, 2, or 3; y is 1, 2, or 3; with the provisos that when x is 1, y is 2 or 3 and when y is 1, x is 2 or 3.

43. The method of claim 42, wherein x is 1 and y is 2 or 3.

44. The method of claim 43, wherein the method further comprises adding a volatile Si—H containing compound to the hyperbranched polymer.

45. The method of claim 44, wherein the volatile Si—H containing compound is selected from the group consisting of trimethylsilane and tetramethyldisiloxane.

46. The method of claim 43, wherein the method further comprises extracting the group VIII metal-containing compounds from the hyperbranched polymer using an immiscible nitrogen-containing polar solvent.

47. The method of claim 46, wherein the polar solvent is selected from the group consisting of tetramethylethylenediamine, polyethylenepolyamine, and acetonitrile.

48. A hyperbranched polymer prepared by the method of claim 44.

49. A hyperbranched polymer prepared by the method of claim 46.

* * * * *